(12) United States Patent
Dragan

(10) Patent No.: US 11,008,595 B2
(45) Date of Patent: May 18, 2021

(54) PROCESS FOR ENZYMATIC PRODUCTION OF TRIGLYCERIDES

(71) Applicant: Stepan Company, Northfield, IL (US)

(72) Inventor: Vladimir Dragan, Garfield, NJ (US)

(73) Assignee: Stepan Company, Northfield, IL (US)

(*) Notice: Subject to any disclaimer, the term of this patent is extended or adjusted under 35 U.S.C. 154(b) by 0 days.

(21) Appl. No.: 16/185,924

(22) Filed: Nov. 9, 2018

(65) Prior Publication Data

US 2019/0078123 A1  Mar. 14, 2019

Related U.S. Application Data

(63) Continuation of application No. PCT/US2017/031087, filed on May 4, 2017.

(60) Provisional application No. 62/340,239, filed on May 23, 2016.

(51) Int. Cl.
*C12P 7/64* (2006.01)
*C07B 41/12* (2006.01)
*C12N 11/02* (2006.01)

(52) U.S. Cl.
CPC ............ *C12P 7/6454* (2013.01); *C07B 41/12* (2013.01); *C12N 11/02* (2013.01)

(58) Field of Classification Search
None
See application file for complete search history.

(56) References Cited

U.S. PATENT DOCUMENTS

| 6,361,980 B2 | 3/2002 | Sugiura et al. |
| 2001/0004462 A1 | 6/2001 | Sugiura et al. |
| 2009/0131701 A1 | 5/2009 | Galante et al. |

OTHER PUBLICATIONS

S.J. Kwon et al. "Production and in situ separation of non- or diacylglycerol catalyzed by lipases in n-hexane", Enzyme and Microbial Technology 17:700-704. (Year: 1995).*
European Patent Office, "extended European search report," issued in connection with patent application No. 17803260.3, dated Jan. 2, 2020, 12 pages.
Wang et al., "Study of Lipozyme TL IM-catalyzed esterification of oleic acid and glycerol for 1,3-diolein preparation," Journal of Molecular Catalysis B; Enzymatic, vol. 127, Nov. 2016, 7 pages.
Phuah et al., "Review on the Current State of Diacylglycerol Production Using Enzymatic Approach," Food Bioprocess Technology, 2015, 18 pages.
Vazquez et al., "Solvent-Free Lipase-Catalyzed Synthesis of Diacylgycerols as Low-Calorie Food Ingredients," frontiers in Bioengineering and Biotechnology, vol. 4, Article 6, Feb. 10, 2016, 10 pages.
Castillo et al., "The Role of Silica Gel in Lipase-Catalyzed Esterification Reactions of High-Polar Substrates," Journal of the American Oil Chemists' Society, vol. 74, No. 2, 1997, 9 pages.
Haas et al., "Lipase-catalyzed synthesis of partial acylglycerols of acetoacetate," European Journal of Lipid Science and Technology, vol. 113, 2011, 12 pages.
Wei et al., "Enzymatic esterification for glycoside lactate synthesis in organic solvent," Enzyme and Microbial Technology, vol. 33, 2003, 5 pages.
Tertykh et al., "Chapter 16: Adsorption and Chemisorption of Enzymes and Other Natural Macromolecules on Silicas," Adsorption on Silica Surfaces, New York, 2000, pp. 524-564.
International Bureau, "International Preliminary Report on Patentability," issued in connection with International Patent Application No. PCT/US2017/031087, dated Dec. 6, 2018, 7 pages.
Abahazi et al. "Additives Enhancing the Catalytic Properties of Lipase from Burkholderia cepacia Immobilized on Mixed-Function-Grafted Mesoporous Silica Gel," Molecules, 2014, 19(7), pp. 9818-9837.
Zhao. "Methods for stabilizing and activating enzymes in ionic liquids—A review," Journal of Chemical Technology & Biotechnology, Jul. 2010, 85, pp. 891-907.
Yeoh et al. "Influence of silica gel in production of diacylglycerol via enzymatic glycerolysis of palm olein," European Journal of Lipid Science and Technology, Jun. 2009, vol. 111, Issue 6, pp. 599-606.
International Searching Authority, "The International Search Report and the Written Opinion," issued in connection with International Application No. PCT/US2017/031087, dated Jul. 27, 2017, 12 pages.

* cited by examiner

*Primary Examiner* — Rebecca E Prouty
(74) *Attorney, Agent, or Firm* — McAndrews, Held & Malloy, Ltd.

(57) ABSTRACT

An enzymatic process for producing fatty acid triglycerides using a lipase catalyst system that includes a mixture of a supported lipase catalyst and an additive, such as silica gel. The additive is used without adsorbing any of the acyl group donor or acyl group acceptor reactants onto the additive. Use of the catalyst system decreases production reaction time, decreases the temperatures required for reaction, and allows for a single reaction vessel. The catalyst system can be used to efficiently produce medium chain triglycerides or conjugated linoleic acid triglycerides.

9 Claims, No Drawings

PROCESS FOR ENZYMATIC PRODUCTION OF TRIGLYCERIDES

RELATED APPLICATIONS

This a continuation of and claims priority to PCT patent application PCT/US17/31087 having an International filing date of May 4, 2017, which claims priority to U.S. Provisional Application No. 62/340,239, filed May 23, 2016. The contents of the applications referred to above are hereby incorporated by reference.

BACKGROUND OF THE INVENTION

The present technology relates to a process for producing fatty acid triglycerides, more specifically an enzymatic process that employs an improved lipase catalyst system. Use of the improved catalyst system decreases production reaction time, decreases the temperatures required for reaction, and allows for a single reaction vessel, thereby decreasing equipment costs.

Triglycerides (or triacylglycerols), are fatty acid esters in which all three of the glycerol —OH groups have been esterified by fatty acids. Some of the many uses of triglycerides include utilization as a fat source in a variety of specialized nutritional products; carriers for flavors, vitamins, essential oils and colors; mineral oil alternatives; moisture barriers; clouding agents for beverages; primary and secondary emollients; lubricants; and solubilizing agents.

Glyceride esters of fatty acids are generally prepared by an esterification reaction of glycerol with a corresponding fatty acid, an alcohol interchange reaction of glycerol with oil or fat, or other similar reactions. Fat-hydrolyzing enzymes, such as various lipases, can be used to catalyze the reaction between fatty acids and/or fatty acid derivatives and glycerol. For example, WO 91/16443 (NovoNordisk AS) discloses a method utilizing *Candida antarctica* lipase, *Candida fugosa* lipase, and other enzymes to catalyze formation of triglycerides from fatty acids or their derivatives in combination with glycerol. One drawback of using an enzyme as a catalyst is that the reaction chamber must be maintained at a temperature conducive to enzymatic catalyzation, typically below 100° C. At such temperatures, the reaction for forming triglycerides typically proceeds at a very slow rate, ill-suited for industrial applications.

To overcome the problem of slow reaction times, U.S. Pat. No. 7,759,096 to Galante et al. discloses an enzymatic process wherein a 1,3 selective lipase is used in a first, low temperature reaction zone to catalyze the formation of 1,3-diglycerides. The 1,3 diglycerides are then isomerized into 1,2-diglycerides in a second, higher temperature reaction zone, and the 1,2-diglycerides are recirculated to the first reaction zone to produce the final triglyceride product. Although Galante et al. demonstrate that faster reaction times are achieved, the process requires multiple reaction zones that utilize different equipment, which can increase manufacturing costs due to the increased cost in equipment needed to conduct the process. In addition, the higher operating temperatures for the second reaction zone require more energy, thereby increasing operating costs.

Therefore a need remains for an efficient process for producing triglycerides that reduces the time required for reaction, but also is cost-effective in terms of equipment costs and energy requirements.

BRIEF SUMMARY OF THE INVENTION

Esters, primarily triglycerides, are manufactured from alcohols, especially polyols, and fatty acids or their short-chain alkyl esters using a novel lipase catalyst system that can significantly reduce the reaction time required to produce the esters. The novel lipase catalyst system comprises a supported lipase catalyst in combination with an additive, such as silica gel, which increases the esterification rate, and consequently reduces the esterification reaction time, compared to a catalyst system that does not employ the additive. Notably, the additive is combined as is with the supported lipase catalyst to produce the lipase catalyst system, without adsorbing any of the reactants onto the additive.

In one aspect, the present technology provides an enzymatic process for preparing esters from a mixture comprising at least one acyl group donor and at least one acyl group acceptor, comprising the steps of:

(a) combining the at least one acyl group donor and the at least one acyl group acceptor in a reactor vessel to form a reaction mixture;

(b) reacting the reaction mixture at a temperature of less than 100° C. in the presence of from 1% to 20% by weight based on the weight of the reaction mixture of a lipase catalyst system to produce the esters, wherein the lipase catalyst system comprises: (i) a non-specific lipase catalyst immobilized on a non-reactive carrier resin, mixed with (ii) an additive, wherein the weight ratio of the lipase catalyst and carrier resin to the additive is about 1:5 to 25:1.

In another aspect, the present technology provides a method for decreasing the reaction time for a lipase-catalyzed esterification reaction of at least one acyl group donor reacted with at least one acyl group acceptor, wherein the method comprises:

(a) combining the at least one acyl group donor and the at least one acyl group acceptor in a reactor vessel to form a reaction mixture;

(b) reacting the reaction mixture at a temperature of less than 100° C. in the presence of from about 1% to about 20% by weight, based on the weight of the reaction mixture, of a lipase catalyst system that comprises (i) an immobilized, non-specific lipase catalyst mixed with (ii) an additive, wherein the weight ratio of the immobilized lipase catalyst to the additive is about 1:5 to about 25:1;

wherein the reaction time for the esterification reaction is less than that of a similar lipase-catalyzed esterification reaction conducted without the additive.

In another aspect, the present technology provides an improved catalyst system for catalyzing an esterification reaction between at least one acyl group donor and at least one acyl group acceptor, wherein the catalyst system comprises (a) a non-specific lipase catalyst immobilized on a hydrophobic carrier, the lipase catalyst comprising from about 10% to about 30% by weight based on the total weight of the catalyst and carrier; and (b) an additive present in an amount such that the weight ratio of (a) to (b) is in the range of about 1:5 to 25:1.

In a further aspect, the present technology provides an improved enzymatic process for preparing triglycerides, such as conjugated linoleic or linolenic acid (CLA) triglycerides, or medium chain triglycerides (MCTs).

Additional features and advantages will be set forth in the detailed description which follows, and in part will be readily apparent to those skilled in the art.

DETAILED DESCRIPTION OF THE PREFERRED EMBODIMENTS

Definitions

A "triglyceride" refers to a triester of glycerol and a fatty acid, or fatty acid derivative thereof, where all three —OH positions on the glycerol triol are esterified. Also as used herein, a triglyceride of a specific fatty acid, such as conjugated linoleic acid, may contain that specific fatty acid at any or all of the three acyl group positions of the triglyceride, while the remaining acyl group positions on the triglyceride are taken up by other fatty acids. Moreover, a triglyceride of a specific fatty acid may contain any of the positional and geometric isomers of that fatty acid.

The term "fatty acid derivative" refers to moieties recognized by one skilled in the art as structures that can be readily converted to carboxylic acids. Examples of such moieties include, but are not limited to: carboxylic acid salts, carboxylic anhydrides, amides, carboxylic esters, ortho esters, 1,3-dioxolanes, dioxanones, oxazoles, and hydrazides.

The term "conjugated linoleic acid" refers to any conjugated linoleic acid or octadecadienoic free fatty acid containing 18 carbon atoms and two double bonds. It is intended that this term encompass all positional and geometric isomers of linoleic acid with two conjugated carbon-carbon double bonds located at any place in the molecule. Similarly, the term "conjugated linolenic acid" refers to any conjugated linolenic acid containing 18 carbon atoms and three double bonds, including all positional and geometric isomers of linolenic acid. The term "CLA" as used herein, collectively encompasses both conjugated linoleic and conjugated linolenic acids. Some examples of CLAs include, but are not limited to the following positional isomers: 7,9-octadecadienoic acid, 9,11-octadecadienoic acid, 10,12-octadecadienoic acid, 11,13-octadecadienoic acid, 9,11,13-octadecatrienoic acid, and 10,12,14-octadecatrienoic acid.

The term "medium chain triglyceride" or "MCT" refers to a triglyceride containing fatty acids with 4 to 12 carbon atoms in the carbon chain of the fatty acid moiety. The term includes both simple triglycerides, which have the same fatty acid at each of the esterified positions, and mixed triglycerides, which have different fatty acids at the esterified positions.

Description

The present technology provides an efficient process for preparing esters from alcohols, especially polyols, and fatty acids or their derivatives, using an improved lipase catalyst system. The lipase catalyst system significantly reduces the reaction time required for the esterification or transesterification reaction, and is particularly useful for preparing triglycerides from a reaction mixture comprising glycerol and fatty acids or their derivatives. The lipase catalyst system comprises a supported lipase catalyst and an additive, such as silica, as described further below.

In the process of the present technology, an acyl group donor, such as a fatty acid or derivative thereof, and an acyl group acceptor, such as glycerol or other polyol, are combined in a stirred reaction vessel under nitrogen to form a reaction mixture. The mole ratio of acyl group donor to acyl group acceptor in the reaction mixture can be in the range of about 5:1 to 1:1, alternatively about 3:1 to 1:1, alternatively about 1.2:1 to 1:1. The catalyst system of the present technology, comprising the supported lipase catalyst and the additive, is also added to the reaction mixture. The catalyst system can be mixed in with the acyl group donor and acyl group acceptor as part of the reaction mixture. Alternatively, the lipase catalyst system can be placed in an external cartridge, such as an enzyme bed, and the reaction mixture can be pumped through the external cartridge one or more times, depending on the reaction conditions.

The reaction mixture is heated to a temperature conducive to enzymatic catalyzation, which is typically below about 100° C. Suitable reaction temperatures are in the range of about 30° C. to about 95° C., alternatively 30° C. to about 90° C., alternatively about 30° C. to about 80° C., alternatively about 30° C. to about 75° C., alternatively about 35° C. to about 70° C., alternatively about 35° C. to about 65° C., preferably about 55° C. to about 75° C. The reaction mixture is stirred and maintained under vacuum pressure in the range of about 20 torr to about 200 torr, alternatively about 45 torr to about 150 torr, alternatively about 50 torr to about 150 torr, alternatively about 50 torr to about 100 torr, until the amount of produced esters, for example triglycerides, is at least 65%, alternatively at least 75%, alternatively greater than 75% by weight based on the composition of the reaction mixture. Due to the presence of the lipase catalyst system, comprising the supported lipase catalyst and the additive, such as silica gel, the reaction proceeds at least two times faster, and in some embodiments about three times faster or more, compared to the reaction time using a supported lipase catalyst alone. Preferably, the total reaction time to prepare the end product esters is less than 36 hours, and more preferably less than 30 hours. By-products of the esterification process, such as water and lower alcohols, can be removed by vacuum, or by any other mechanism known in the art, such as free evaporation or the use of molecular sieves or filters.

The lipase catalyst of the present technology can be any suitable non-specific lipase catalyst. By "non-specific" is meant that the lipase can esterify fatty acids on any position of the glycerol or polyol backbone. Suitable lipases include *Candida antartica* (CAL-B lipase), *Candida cylindracea, Candida rugosa, Burkholderia* lipases, *Pseudomonas* lipases and other lipases. It is also preferred that the lipase enzyme be immobilized on a suitable support. Immobilized enzymes are preferred in order to prevent disposing of the enzyme along with reaction by-products. Immobilized enzymes also allow the same enzyme catalyst system to be used in multiple runs of the process. Supports for immobilizing a lipase enzyme are known in the art and include supports made from polyacrylates, polyethylene, polypropylene, polystyrene, metal oxides, ceramics, zeolites, and others. Useful herein are supports that are hydrophobic and non-reactive with the reaction mixture components, such as an acrylic resin, preferably a macroporous acrylic resin. The amount of lipase catalyst on the support can range from about 10% to about 30% by weight, based on the total weight of the supported catalyst. The support comprises about 70% to about 90% by weight of the supported catalyst. An example of a suitable commercially available lipase catalyst for use in the present catalyst system is Lipozyme® 435, an acrylic-supported CAL-B lipase, available from Novozyme.

The catalyst system also comprises an additive, such as, for example, silica alumina produced by the precipitation of amorphous alumina onto an amorphous silica gel, or a silica gel additive. Useful particle sizes for the silica gel are in the range of about 5 µm to about 500 µm, alternatively from about 20 µm to about 200 µm. The weight ratio of the supported lipase catalyst to the additive in the catalyst system can range from about 1:5 to 25:1, alternatively 1:3 to 22:1. Useful amounts of the catalyst system (supported catalyst and additive) in the reaction mixture range from about 1% to about 20% by weight based on the total weight of the reaction mixture, alternatively about 1 to about 10% by weight, alternatively about 1% to about 5% by weight.

Surprisingly, it has been found that the concentration of the additive in the reaction mixture has an important effect on the reaction rate of the esterification. For example, useful amounts of silica gel range from about 0.02% to about 5%, alternatively 0.04% to 1.5% by weight, based on the total weight of the reaction mixture. Amounts of silica gel above 5% by weight have been found to inhibit the glycerol esterification process.

It has also been found that there is no need to adsorb either the lipase catalyst or the acyl group acceptor reactant onto the silica gel additive in order to achieve reduced reaction times. Simply adding the silica gel, as is, to the supported lipase catalyst results in about a three-fold increase in glycerol esterification rates compared to use of a supported lipase catalyst alone. This result is surprising because the literature suggests that adsorption of glycerol onto a silica gel support is required for suitable esterification reaction times, and that poor acid conversion rates (esterification) occur when free glycerol, rather than silica-adsorbed glycerol, is used. Immobilizing the lipase catalyst on the silica gel, instead of using an acrylic support, does not lead to improved reaction rates compared to those achieved by an acrylic-supported lipase alone.

The fatty acids or their derivatives for use in producing the triglycerides can be any type of saturated or unsaturated, linear or branched, fatty acids containing 2 to 24 carbon atoms, preferably 4 to 20 carbon atoms. Types of fatty acids which may be used include, but are not limited to: butyric acid, valeric acid, caprionic acid, caprylic acid, capric acid, enanthic acid, pelargonic acid, undecanoic acid, lauric acid, linoleic acid, linolenic acid, myristic acid, palmitic acid, zoomaric acid, stearic acid, oleic acid, elaidic acid, arachidonic acid, eicosapentaenoic acid, and docosahexaenoic acid. Additionally, lower alkyl (C1 to C4) esters and other fatty acid derivatives may also be used, including carboxylic acid salts, carboxylic anhydrides, amides, carboxylic esters, ortho esters, 1,3-dioxolanes, dioxanones, oxazoles, and hydrazides.

One embodiment of the present technology utilizes conjugated linoleic or linolenic acids (collectively termed "CLA") as the acyl group donor. U.S. Pat. No. 6,420,577 (Reaney, et al.) describes a process for making CLAs by reacting a linoleic acid-rich oil with a base, while in the presence of a catalytic amount of such a base in an aqueous medium via simultaneous hydrolysis and isomerization. Alternatively, CLAs may also be produced by conversion of the linoleic acid-rich oil to an alkyl ester which is further purified using a conventional method (usually distillation), with subsequent isomerization of the ester, or any other method known to those skilled in the art.

Any geometric or positional isomers of CLA may be utilized as the fatty acid in the present technology, however, the cis-9, trans-11 and trans-10, cis-12 isomers of CLA are preferred. The resultant triglyceride may contain CLA derived acyl groups on one, two, or all three of the glycerol backbone positions, with other fatty acids contained on any remaining positions. Preferably, however, the triglycerides produced by the presently described process contain at least 80% and more preferably at least 90% CLA derived acyl groups. The purity of the CLA content may be confirmed via Nuclear Magnetic Resonance Spectroscopy.

A further embodiment of the present technology utilizes medium chain fatty acids as the acyl group donor. Typical sources of medium chain fatty acids include fractionated coconut oil and fractionated palm kernel oil which contain significant amounts of C8 (caprylic) and C10 (capric) carbon chains. The MCTs produced by the present process are free, or substantially free, of process contaminants that are found in MCTs produced by conventional, high temperature processes that do not use a lipase catalyst. The term "substantially free" as used herein means levels of process contaminants that are less than about 1 to 2 ppm.

It will be appreciated by those skilled in the art that other fatty acids or their esters, such as omega-3 fatty acids or ethyl esters, can be used as the acyl group donor in the process of the present technology. It will also be appreciated that polyols other than glycerol, such as glucose, sucrose or erythritol, can be used as the acyl group acceptor for the esterification reaction.

The presently described technology and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appended to this specification, and any alterations, modifications, or equivalents of those claims.

EXAMPLES

Example 1. (Comparative) CLA Triglycerides with Standard Lipase Catalyst

CLA methyl esters and glycerin (90 mol %) were combined under nitrogen in a stirred reaction vessel and heated to 60-65° C. with Lipozyme® 435, an acrylic supported CAL-B lipase available from Novozyme. The amount of Lipozyme® 435 was 0.5% wt based on enzyme, 2.4% wt based on supported enzyme. The reaction was held under vacuum (50 torr) with stirring for 69 to 72 hours, until the triglyceride specification was reached (>75% of total glycerides by GC). Unreacted methyl esters were removed under vacuum to give the final CLA triglyceride product.

Example 2. CLA Triglycerides with Improved Catalyst System

CLA methyl esters and glycerin (90 mol %) were combined under nitrogen in a stirred reaction vessel and heated to 60-65° C. with the following catalyst system: Lipozyme® 435 (from Novozyme, 0.5% wt based on enzyme, 2.4% wt based on supported enzyme) mixed with 1% wt (30-60 µm) silica gel. The reaction was held under vacuum (50 torr) with stirring for 19 to 23 hours, until the triglyceride specification was reached (>75% of total glycerides). Unreacted methyl esters were removed under vacuum to give the final CLA triglyceride product.

A comparison of Example 1 with Example 2 shows the addition of silica gel to the catalyst system significantly decreases the reaction time, about a three-fold decrease, for preparing the CLA triglycerides.

Example 3. CLA Triglycerides from Acids with Improved Catalyst System

Conjugated linoleic acids (1360 g) and glycerin (122.9 g) were combined under nitrogen in a stirred reaction vessel and heated to 60-65° C. with 50 g of a catalyst system prepared by stirring together 2.6 parts of Lipozyme® 435 with 1 part of (30-60 µm) silica. The reaction was held under vacuum (50 torr) with stirring for 7 h, until triglycerides formed >75% by weight of the reaction mixture as determined by gas chromatography (GC). After filtration to remove the catalyst, unreacted fatty acids were removed under vacuum to give the final product.

Example 4. Medium Chain Triglycerides from Esters with Standard Catalyst System A mixture of methyl caprate and methyl caprylate (153.21 g, 0.90 moles) and glycerol (25.12 g, 0.27 moles) were combined in a 250 mL r.b. flask with a Teflon paddle mechanical stirrer (300 rpm), thermowell, N2 inlet and overhead recovery system. The reaction mixture was heated to 65° C. under nitrogen. When the temperature reached 65° C., Lipozyme® 435 (1.76 g, immobilized CAL B enzyme) was added and pressure was reduced to 245 mm Hg. The reaction mixture was sampled at 5.5 hours after the addition of the enzyme. The samples were analyzed by GC. The analysis showed 19.5% of the glycerol had been esterified.

Example 5. Medium Chain Triglycerides from Esters with Improved Catalyst System A mixture of methyl caprate and methyl caprylate (153.47 g, 0.90 moles) and glycerol (25.31 g, 0.27 moles) were combined in a 250 mL r.b. flask with a Teflon paddle mechanical stirrer (300 rpm), thermowell, N2 inlet and overhead recovery system. The mixture was heated to 65° C. under nitrogen. When the temperature reached 65° C., silica gel (0.08 g) and Lipozome® 435 (1.76 g, immobilized CAL B enzyme) were added and the pressure was reduced to 235 mm Hg. The reaction mixture was sampled at 5.5 hours after the addition of the enzyme. The samples were analyzed by GC. The analysis showed 41.9% of the glycerol had been esterified. This is a significant improvement of the transesterification rate when compared to the standard enzyme system.

The present technology is now described in such full, clear and concise terms as to enable a person skilled in the art to which it pertains, to practice the same. It is to be understood that the foregoing describes preferred embodiments of the present technology and that modifications may be made therein without departing from the spirit or scope of the present technology as set forth in the appended claims. Further the examples are provided to not be exhaustive but illustrative of several embodiments that fall within the scope of the claims.

What is claimed is:

1. An enzymatic process for preparing esters from a mixture comprising at least one acyl group donor and at least one acyl group acceptor, comprising the steps of:
    (a) combining the at least one acyl group donor and the at least one acyl group acceptor in a reactor vessel to form a reaction mixture, wherein the at least one acyl group donor comprises fatty acids, derivatives thereof, or mixtures thereof;
    (b) reacting the reaction mixture at a temperature of less than 100° C. in the presence of from about 1% to about 520% by weight based on the weight of the reaction mixture of a lipase catalyst system to produce the esters, wherein the lipase catalyst system comprises a mixture of:
        (i) non-specific lipase catalyst immobilized on a non-reactive hydrophobic carrier resin, the lipase catalyst being selected from the group consisting of *Candida Antarctica, Candida cylindracea, Candida rugosa, Burkholderia lipases, Pseudomonas* lipases, and combinations thereof, and present in an amount of about 10% to about 30% by weight based on the total weight of the lipase and the carrier resin; and
        (ii) a silica gel or silica/alumina additive, wherein the weight ratio of the lipase catalyst and carrier resin to the additive is about 1:5 to about 25:1, and the amount of the silica gel or silica/alumina additive in the reaction mixture is about 0.04% to about 1.5% by weight of the reaction mixture.

2. The process of claim 1, wherein the acyl group donor comprises fatty acids having from 4 to 12 carbon atoms, derivatives thereof or mixtures thereof, and the acyl group acceptor comprises glycerol.

3. The process of claim 1, wherein the acyl group donor comprises conjugated linoleic acids, derivatives thereof, or mixtures thereof, and the acyl group acceptor comprises glycerol.

4. The process of claim 1, wherein the non-reactive carrier resin is an acrylic resin.

5. The process of claim 1, wherein the reaction mixture is reacted at a temperature of about 55° C. to about 75° C.

6. The process of claim 1, wherein the reaction mixture is reacted at a vacuum pressure of about 20 torr to about 200 torr.

7. The process of claim 1, wherein the silica gel has a particle size of about 5 μm to about 500 μm.

8. The process of claim 1, wherein the acyl acceptor is not adsorbed onto the additive prior to introducing the catalyst system to the reaction mixture.

9. The process of claim 1, wherein the non-specific lipase catalyst is *Candida Antarctica* lipase B.

* * * * *